US012758348B2

(12) United States Patent
Gawel et al.

(10) Patent No.: US 12,758,348 B2
(45) Date of Patent: Oct. 13, 2026

(54) UNIVERSAL TRACKING ARRAY APPARATUS

(71) Applicant: SYNAPTIVE MEDICAL INC., Toronto (CA)

(72) Inventors: Rob Gawel, Etobicoke (CA); Shawana Habib, North York (CA); Brett Tapson, Sydney (AU); Kyle Richard Dupont, Toronto (CA)

(73) Assignee: SYNAPTIVE MEDICAL INC., Mississauga (CA)

( * ) Notice: Subject to any disclaimer, the term of this patent is extended or adjusted under 35 U.S.C. 154(b) by 330 days.

(21) Appl. No.: 18/415,121

(22) Filed: Jan. 17, 2024

(65) Prior Publication Data

US 2024/0238063 A1 Jul. 18, 2024

Related U.S. Application Data

(60) Provisional application No. 63/480,185, filed on Jan. 17, 2023.

(51) Int. Cl.
*A61B 90/00* (2016.01)
*A61B 34/20* (2016.01)

(52) U.S. Cl.
CPC .............. *A61B 90/08* (2016.02); *A61B 34/20* (2016.02); *A61B 2090/0807* (2016.02)

(58) Field of Classification Search
CPC . A61B 90/08; A61B 34/20; A61B 2090/0807; A61B 2017/00477; A61B 2034/2055; A61B 2090/3983
See application file for complete search history.

(56) References Cited

U.S. PATENT DOCUMENTS

| | | | | |
|---|---|---|---|---|
| 5,176,702 | A * | 1/1993 | Bales | A61B 17/320016 81/319 |
| 7,840,256 | B2 * | 11/2010 | Lakin | A61B 90/39 600/421 |
| 8,182,469 | B2 * | 5/2012 | Anderson | A61B 90/57 606/1 |
| 8,974,380 | B2 * | 3/2015 | Michaeli | A61B 17/0293 600/233 |
| 12,484,972 | B2 * | 12/2025 | Coakley | A61B 34/20 |
| 2005/0215888 | A1 * | 9/2005 | Grimm | A61B 90/39 606/130 |
| 2006/0281991 | A1 * | 12/2006 | Fitzpatrick | A61B 90/14 600/426 |
| 2011/0208006 | A1 * | 8/2011 | Michaeli | A61B 17/0293 600/219 |
| 2015/0351771 | A1 * | 12/2015 | Malkowski | A61B 17/1285 606/143 |
| 2022/0346844 | A1 * | 11/2022 | Dewey | A61B 90/39 |
| 2024/0374324 | A1 * | 11/2024 | Ghanam | A61B 34/20 |

* cited by examiner

*Primary Examiner* — Michael J Lau

(57) ABSTRACT

A universal tracking array apparatus that can be attached to various tools, e.g., surgical instruments, to enable the tools to be tracked, e.g., with a surgical navigation system. The apparatus includes first and second clamp bodies with a ratcheting mechanism to couple the bodies together and form a clamp to retain the instrument. The first clamp body also supports a tracking array, and can support the tracking array in a plurality of selectable positions.

12 Claims, 6 Drawing Sheets

UNIVERSAL TRACKING ARRAY APPARATUS

CROSS-REFERENCE TO RELATED APPLICATIONS

This application claims priority from U.S. provisional patent application No. 63/480,185, filed Jan. 17, 2023, the contents of which is incorporated herein by reference.

FIELD

The specification relates generally to surgical navigation systems, and specifically to a tracking apparatus for surgical navigation systems.

BACKGROUND

Various instruments may be used by surgeons and/or other staff during a surgical procedure. Such instruments may be tracked, to monitor the position of an instrument relative to a patient, other instruments, or the like. Tracking an instrument may involve detecting, e.g., via one or more cameras, fiducial markers affixed to the instrument. Due to the wide variety of instruments used during such procedures, however, designing and fabricating such instruments with fiducial markers can be costly and time-consuming.

SUMMARY

Examples disclosed herein are directed to an apparatus comprising: a tracking array having a plurality of fiducial markers; a first clamp body having: (i) a mounting surface configured to support the tracking array; (ii) a first fastener; and (iii) a first clamping surface; and a second clamp body having: (i) a second fastener complementary with the first fastener, the second fastener configured to engage with the first fastener to couple the first clamp body to the second clamp body; (ii) a second clamping surface configured, when the second clamp body is coupled with the first clamp body, to define a clamping jaw for retaining an instrument.

BRIEF DESCRIPTIONS OF THE DRAWINGS

Embodiments are described with reference to the following figures.

Figure 1A:
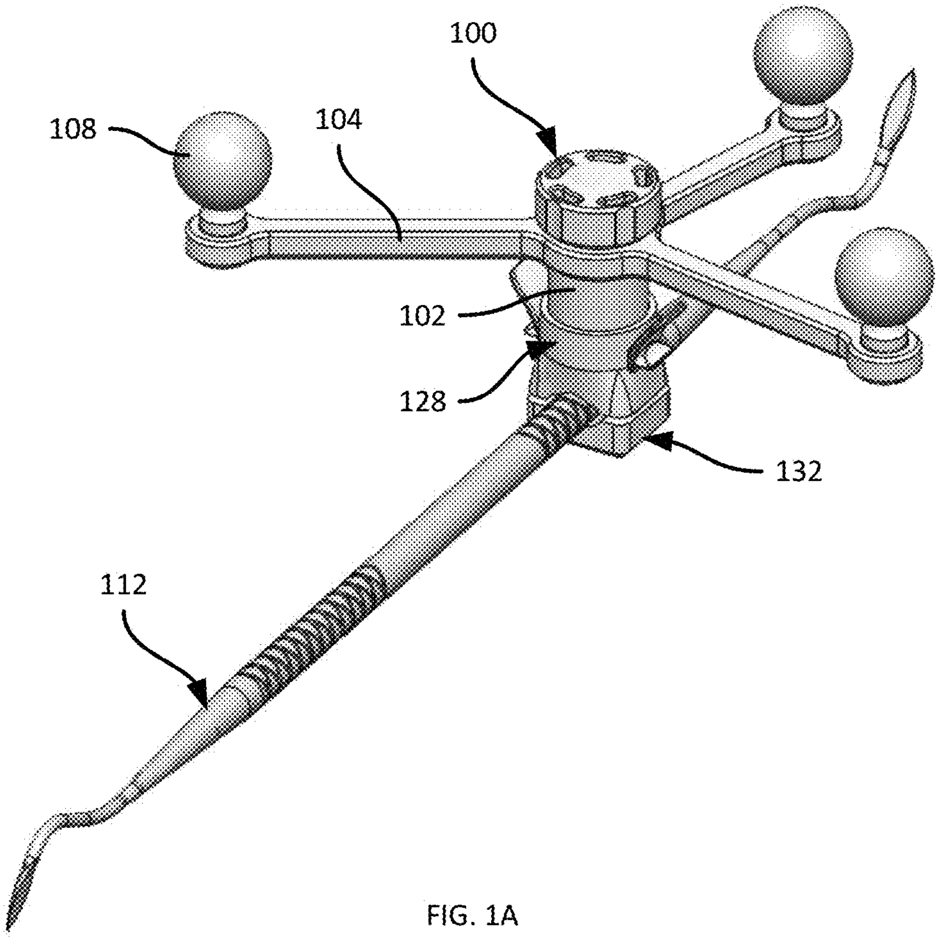
FIG. 1A is a perspective view of a universal tracking array apparatus.

FIGS. 6A, 6B, 6C, 6D, 6E, and 6F are diagrams illustrating selectable positions for the tracking array that are provided by the apparatus of FIG. 1A.

DETAILED DESCRIPTION

Figure 1B:
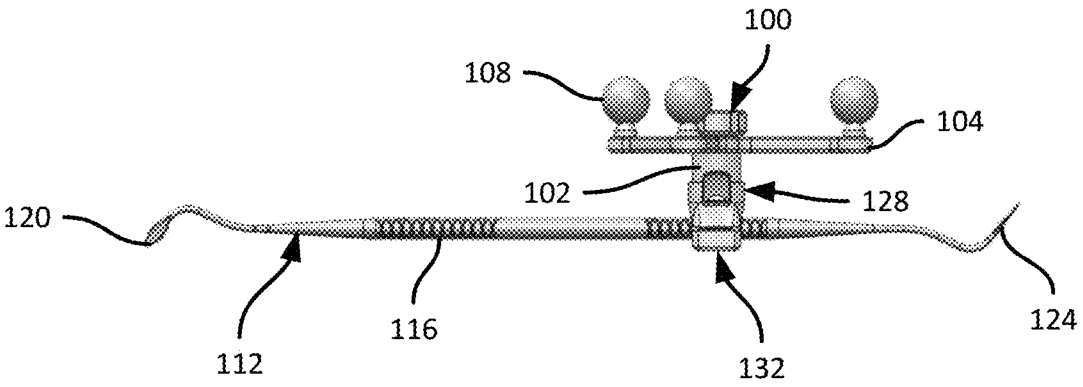
FIG. 1B is a side view of the universal tracking array apparatus of FIG. 1A.

FIGS. 1A and 1B depict a universal tracking array apparatus 100, also referred to simply as the apparatus 100. The apparatus 100 includes a tracking array including a body 102 supporting a frame 104, and a plurality of fiducial markers 108 (e.g., retro-reflective markers or the like) supported on the frame 104, e.g., at the ends of the arms. In this example, the frame 104 includes three arms, each supporting a fiducial marker 108 on an end thereof. A wide variety of other structures are also contemplated for the tracking array, including greater or smaller numbers of markers 108, and other shapes of frame 104.

The tracking array, and specifically the markers 108, are configured to be detectable by motion tracking systems such as depth cameras equipped with infrared emitters or the like. As will be apparent to those skilled in the art, capturing a sequence of images and detecting the positions of the markers 108 in the images permits such systems, based on the relative positions of the markers 108 within each image and the shifting positions of the markers 108 from image to image, to monitor the position and orientation of the tracking array. Such tracking systems can therefore also, by inference from the position and orientation of the tracking array, monitor the position and orientation of other objects affixed to the tracking array, such as a surgical instrument 112. The position and orientation of the instrument 112 (or any other suitable object with a tracking array affixed thereto) can be employed for various purposes, such as in the operation of a surgical navigation system to illustrate the instrument 112 in relation to patient tissue, diagnostic images, a previously planned trajectory for the instrument, and the like.

The instrument 112 may be one of many employed during a surgical procedure (or any of a variety of other procedures, such as manufacturing processes or the like, during which tracking of instruments and/or tools may be desired). Monitoring the position and orientation of the instrument 112 is dependent on a fixed physical relationship between the tracking array and the instrument 112. Some trackable instruments therefore include integrated tracking arrays. Integrated tracking arrays, however, may increase the cost and complexity of the instrument 112, which may in turn complicate sourcing the instrument 112. Integrating a tracking array with the instrument 112 may also complicate cleaning of the instrument 112 in preparation for a further procedure.

The apparatus 100 is therefore configured to removably affix the tracking array to any of a variety of instruments and/or tools, including the instrument 112. The apparatus 100 can be attached to the instrument 112 so as to place the tracking array in a fixed spatial relationship relative to the instrument 112, and later removed from the instrument 112, e.g., for washing, disposal, or the like. The apparatus 100 can be adapted to any of a variety of instruments, and any suitable instrument can therefore be retrofitted with a tracking array via the apparatus 100. Further, as discussed below, the position of the arms of the frame 104 and therefore of the markers 108 can be selected to mitigate interference with an operator of the instrument 112. For example, as shown in FIG. 1B, in one mode of operation, the instrument 112 may be held by an operator at the textured portion 116, e.g., to contact patient tissue with a first end 120 of the instrument 112. The apparatus 100, for this mode of operation, may therefore be affixed to the instrument 112 closer to an opposite end 124 of the instrument than to the end 120, leaving the portion 116 relatively unencumbered. The apparatus 100 can be fabricated from lightweight materials such as plastics or other suitable polymers, e.g., to mitigate the effects of the apparatus 100 on the weight and balance of the instrument 112. The apparatus 100 can be manufactured via injection molding, 3D printing, or the like. The apparatus 100, in other words, may be relatively inexpensive in comparison with the instrument 112.

The apparatus 100 includes, in addition to the tracking array, a first clamp body 128 and a second clamp body 132. Although the first clamp body 128 can be referred to as an "upper" clamp body, and the second clamp body can be referred to as a "lower" clamp body, the instrument 112 may be operated in a wide variety of orientations, and the orientations shown in the accompanying drawings are purely for the purpose of explanation.

The first clamp body 128 includes a mounting surface configured to support the tracking array (in particular, the body 102 of the tracking array). The first clamp body 128 also includes a first fastener, configured to engage with a second fastener of the second clamp body 132 to couple the clamp bodies 128 and 132 together. The clamp bodies 128 and 132 also include respective clamping surfaces that cooperate, when the clamp bodies 128 and 132 are coupled, to form a clamping jaw to retaining the instrument 112 therein, as shown in FIG. 1A. The mounting surface and fasteners are described in greater detail below.

Figure 2A:
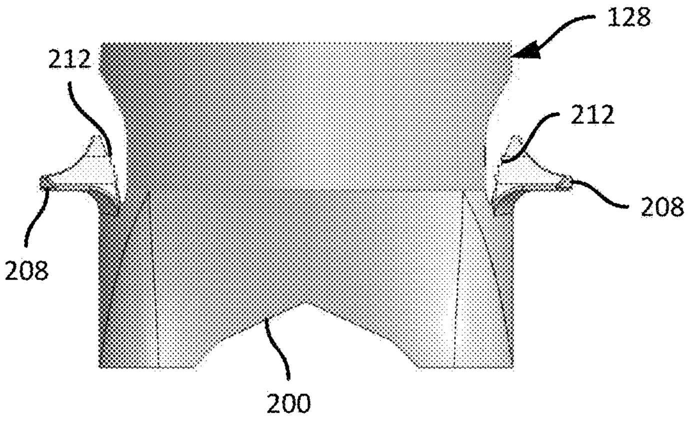
FIG. 2A is a side view of a first clamp body of the apparatus of FIG. 1A.

FIG. 2A is a side view of the first clamp body 128, illustrating a first clamping surface 200 thereof. The first clamping surface 200 can include one or more pairs of inclined surfaces (two pairs of inclined surfaces are shown in this embodiment), enabling the first clamping surface 200, or at least a portion thereof, to engage instruments with a variety of diameters. In some examples, the apparatus 100 may be produced in different sizes, e.g., with a first size configured to accept instruments with shaft diameters between 1 and 5 mm, a second size configured to accept instruments with shaft diameters between 5 and 10 mm, and so on.

Figure 2B:
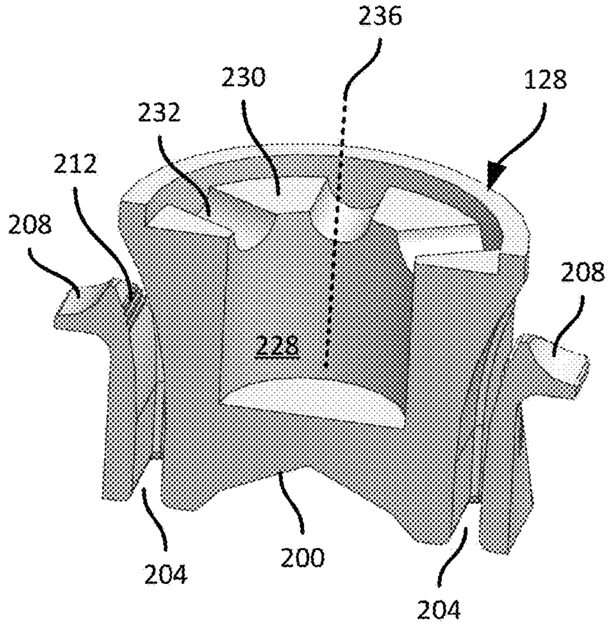
FIG. 2B is a cross section of the first clamp body of the apparatus of FIG. 2A.

As illustrated in FIG. 2A and the cross-section of FIG. 2B, the first clamp body 128, in this example, includes fasteners in the form of a pair of slots 204 extending from an end of the body 128, within a side wall of the body 128, to respective exits on the sides of the body 128. The fasteners also each include a tongue 216 corresponding to each slot 204, e.g., disposed at the exit of each slot 204, and including teeth 212.

Figure 2C:
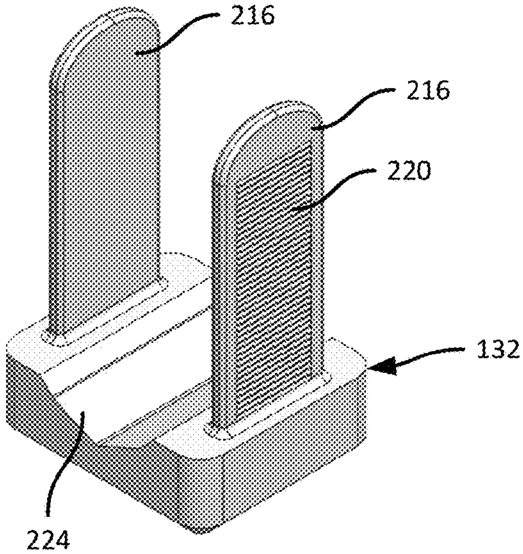
FIG. 2C is a perspective view of a second clamp body of the apparatus of FIG. 1A.

FIG. 2C illustrates the second clamp body 132 in isolation. The slots 204 of the body 128 are configured to receive corresponding tongues 216 of the body 132, shown in FIG. 2C. Each tongue 216 includes a serrated outer surface 220, configured to engage with the teeth 212 on the corresponding tab 208. The teeth 212 permit the tongue 216 to insert into the slot 204, but prevent the tongue 216 from being withdrawn from the slot 204. In some examples, the tabs 208 are deformable, and can be manipulated to pull the tabs 208 outwards, releasing the tongues 216, e.g., to dismantle the apparatus 100. In the absence of such pulling, the tabs 208 retain the tongues 216 within the slots 204, and the body 132 can therefore be ratcheted onto the body 128, clamping the instrument 112 between the clamping surface 200 and a second clamping surface 224 of the body 132.

A wide variety of other fasteners can also be employed for coupling the bodies 128 and 132, including screws, bolts, adhesives, or the like. In further examples, the slot and tongue mechanism shown in FIGS. 2A, 2B, and 2C can be used, but the tabs can be disposed on the body 128, and the slots can be disposed on the body 132.

The body 128 can also include, as shown in FIG. 2B, a chamber 228, e.g., to accommodate a nut or other anchoring structure to receive a fastener such as a bolt, affixing the tracking array (specifically, the body 102 of the tracking array) to the first clamp body 128. The first clamp body 128 can also include a mounting surface 230 having a plurality of guide structures 232 arranged about an axis 236 of the first clamp body 128. The guide structures 232, which in the illustrated example include radial grooves (e.g., grooves into the mounting surface 230, arranged radially about the axis 236), are configured to cooperate with one or more complementary guide structures of the body 102, such as a protrusion configured to extend into the grooves 232. The guide structures are configured to maintain the tracking array at one of a set of predetermined angles relative to the body 128. In the present example, the guide structures 232 define six distinct orientations for the tracking array relative to the body 128.

Figure 3:
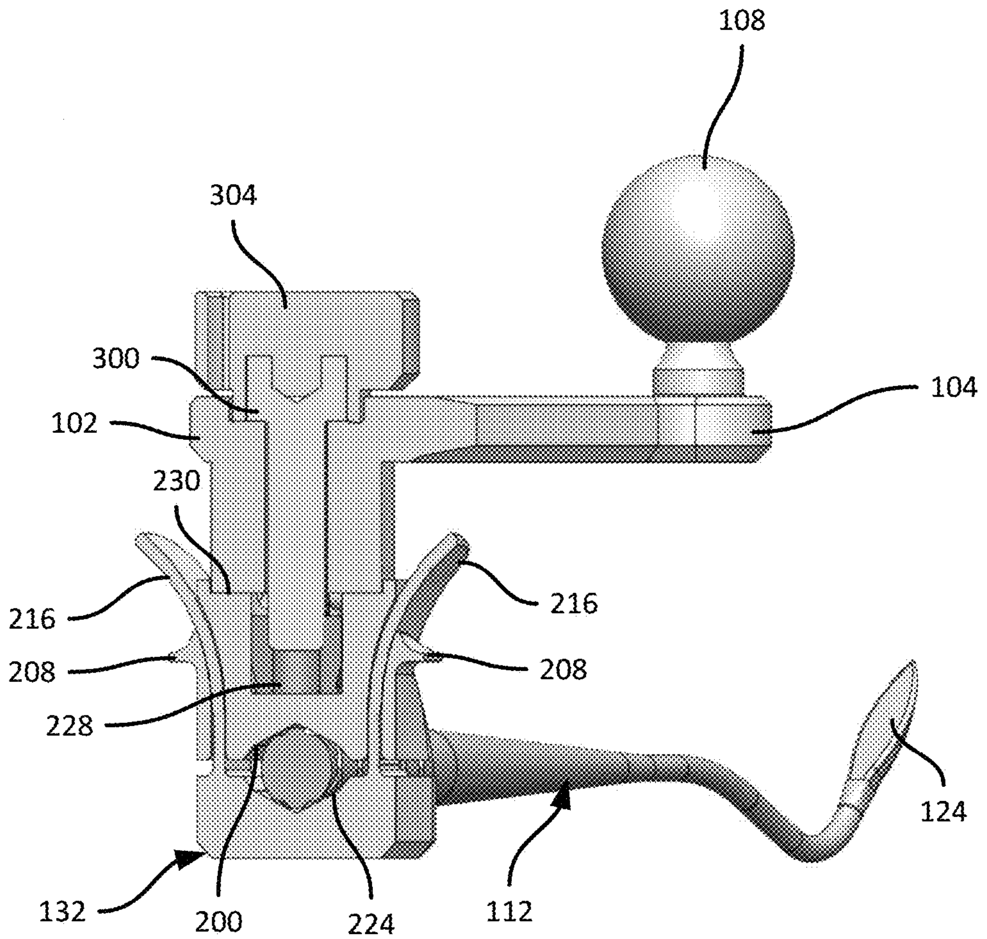
FIG. 3 is a cross section of the apparatus of FIG. 1A.

FIG. 3 is a cross-sectional view of the apparatus 100, illustrating the tongues 216 extending through the slots 204 to be engaged by the teeth 212 of the tabs 208, retaining the second clamp body 132 against the first clamp body 128. The clamping surfaces 200 and 224 then form a clamping jaw retaining the instrument 112 in a fixed position relative to the apparatus 100. As also shown in FIG. 3, the body 102 of the tracking array can include an opening therethrough for receiving a fastener such as a bolt 300, which can engage with a nut or other anchor in the chamber 228 (the nut is omitted from FIG. 3). In the illustrated example, the apparatus 100 also includes a cap 304 configured to engage with a head of the bolt 300, to facilitate manual (e.g., toolless) tightening and loosening of the bolt 300.

Figure 4A:
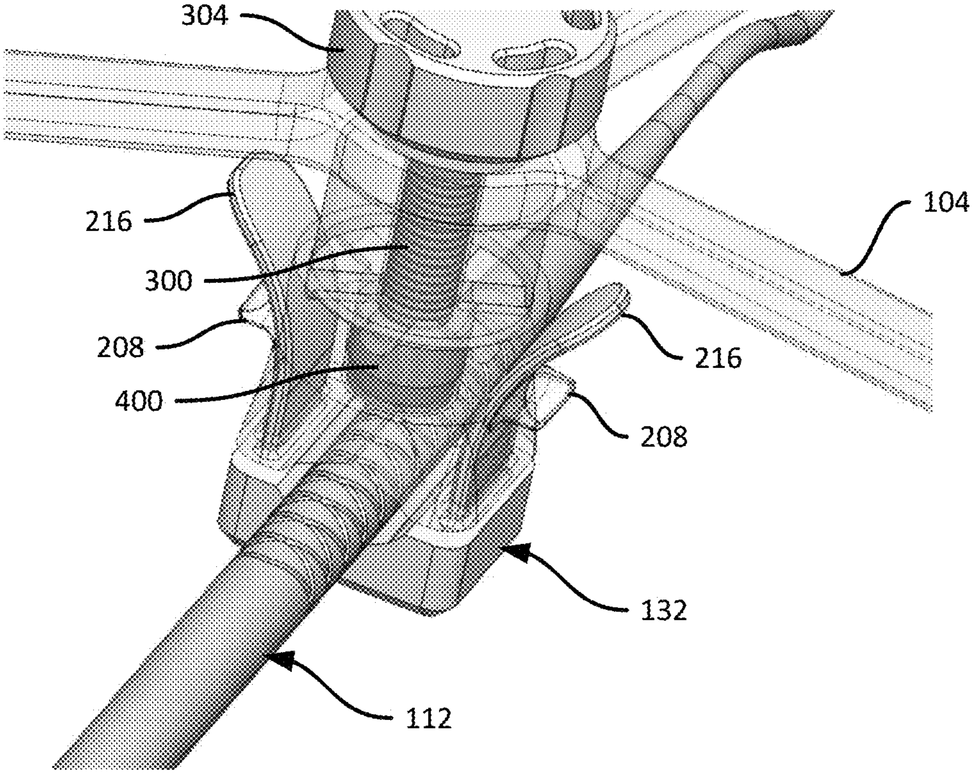
FIG. 4A is a partial wireframe view of the apparatus of FIG. 1A.
Figure 4B:
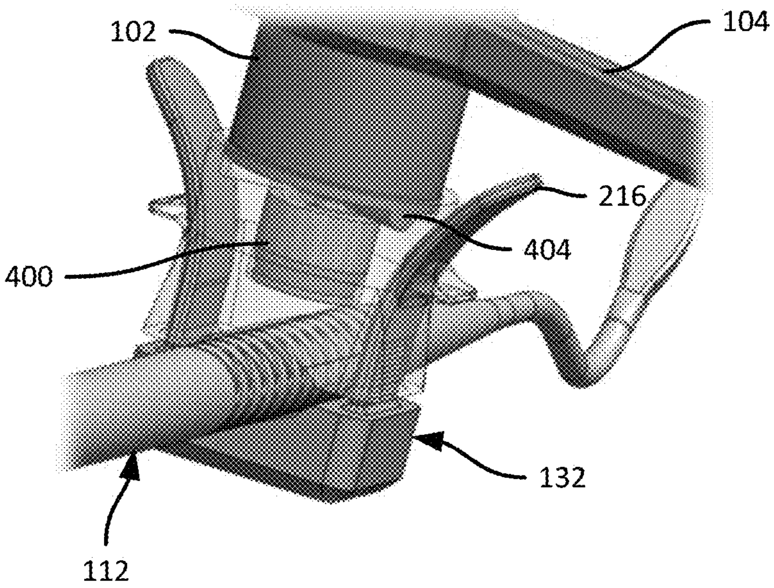
FIG. 4B is another partial wireframe view of the apparatus of FIG. 1A

FIG. 4A and FIG. 4B are partial wireframe views of the apparatus 100, revealing a nut or other suitable anchor 400 within the chamber 228, into which the fastener 300 is configured to extend to affix the body 102 of the tracking array to the first clamp body 128. The nut 400 can be affixed within the chamber 228, e.g., via suitable adhesive, via integral formation with the body 128, or the like. Also shown in FIG. 4B is a complementary guide structure 404 of the body 102, in the form of a rib or other suitable protrusion engaged with a guide structure 232 of the mounting surface 230.

Figure 5:
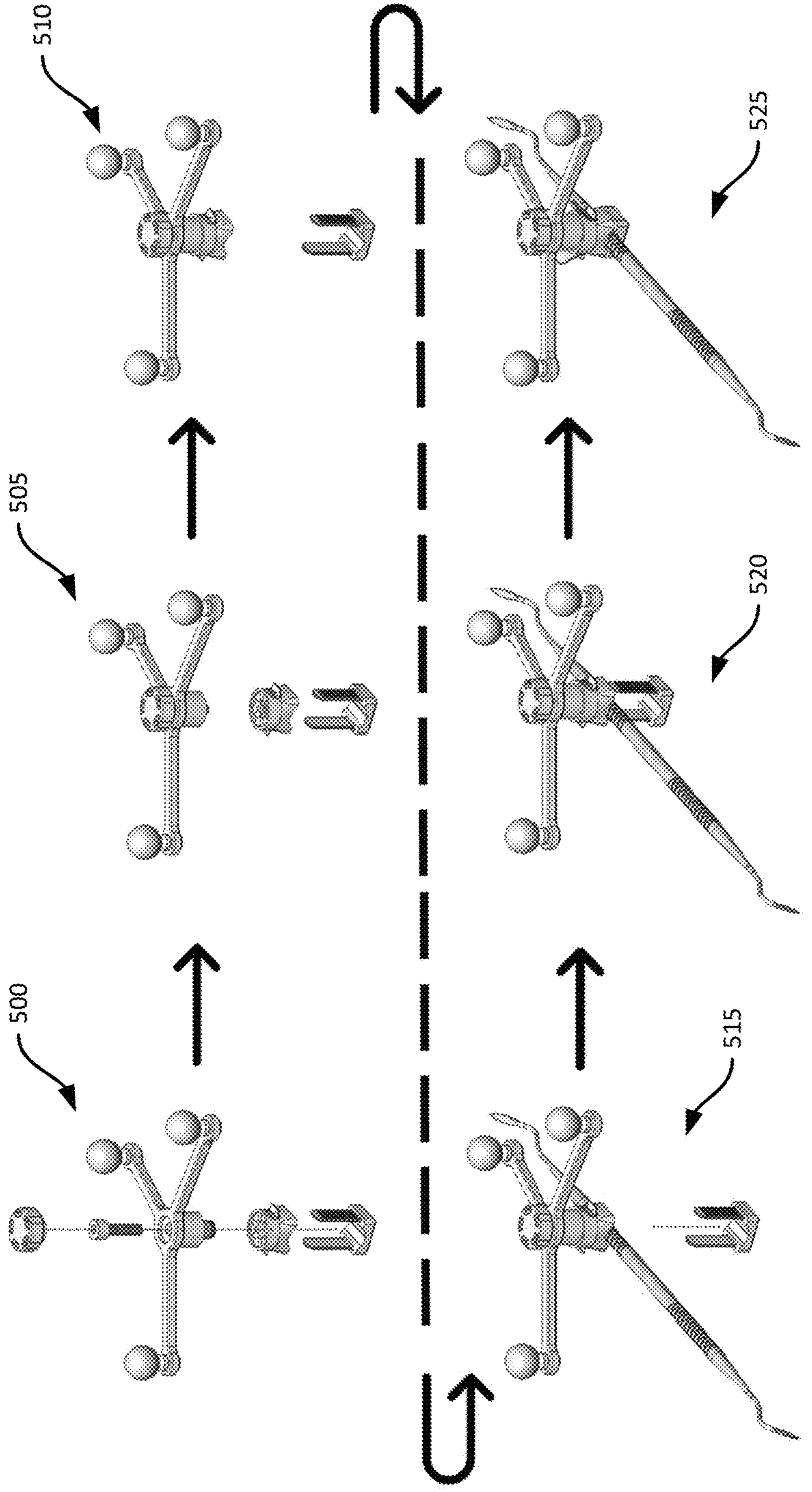
FIG. 5 is a diagram illustrating an assembly process for the apparatus of FIG. 1A.

FIG. 5 illustrates an assembly process for the apparatus 100. In a first stage 500, the components of the apparatus 100 are shown separated from one another, e.g., with the cap 304, fastener 300, tracking array, body 128, and body 132 physically separate. In a second stage 504, the fastener 300 can be inserted through the body 102 of the tracking array, and the cap 304 can be placed onto the fastener 300. In a third stage 510, the tracking array, cap 304 and fastener 300 can be affixed to the first clamp body 128, selecting an angular position for the tracking array using the guide structures discussed above.

In a fourth stage 515, the instrument 112 is placed against the first clamping surface 200 of the first clamp body 128. In a fifth stage 520, the second clamp body 132 is engaged with the first clamp body 128, by inserting the tongues 216 into the slots 204. In a sixth stage 525, the second clamp body 132 is ratcheted onto the first clamp body until the instrument 112 is firmly retained between the clamping surfaces 200 and 224.

FIGS. 6A-6F illustrates the plurality of predetermined positions at which the tracking array can be maintained relative to the instrument 112 by the apparatus 100. By selecting which guide structures to engage between the body 102 and the mounting surface 230, the tracking array can be placed at various angles, in this example separated by increments of 60 degrees. For example, in FIG. 6A the tracking array is placed at an angle of zero degrees relative to the instrument 112 (e.g., in that a primary arm 104*a* is at an angle of zero degrees with a forward portion of the instrument 112 carrying the portion 116.

Figure 6A:
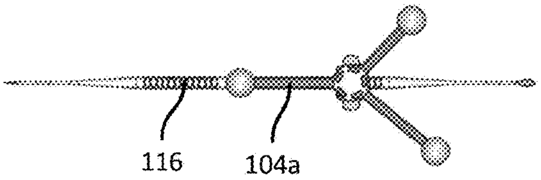
Figure 6B:
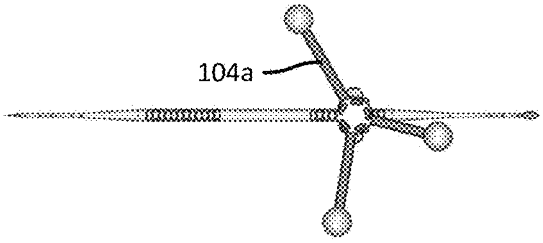
Figure 6C:
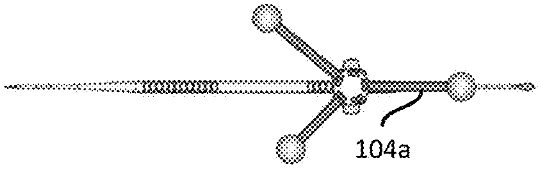
Figure 6D:
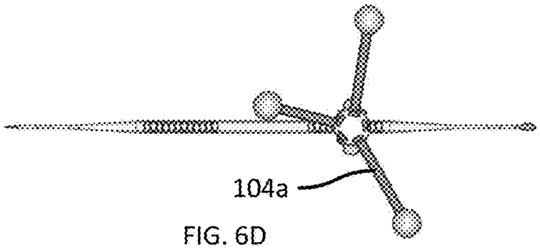
Figure 6E:
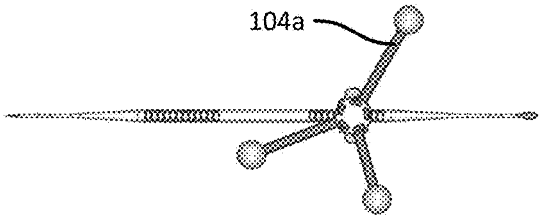
Figure 6F:
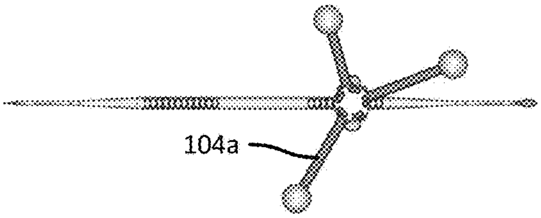

In FIG. 6B, the primary arm 104*a* is at an angle of 60 degrees relative to the instrument 112. In FIGS. 6C, 6D, 6E, and 6F respectively, the primary arm 104*a* is at an angle of 120, 180, 240, and 300 degrees, respectively. As will be apparent, the mounting surface 230 can be provided with other guide structures, e.g., disposed at other sets of angles, to increase or decrease the breadth of orientations provided by the apparatus 100. In some examples, the orientations provided by the apparatus 100 need not be equally spaced, as in this example.

The scope of the claims should not be limited by the embodiments set forth in the above examples, but should be given the broadest interpretation consistent with the description as a whole.

The invention claimed is:

1. An apparatus, comprising:
- a tracking array having a plurality of fiducial markers;
- a first clamp body having:
  - a mounting surface configured to support the tracking array, the mounting surface including a plurality of radial guide grooves arranged about an axis of the first clamp body, the radial guide grooves configured to define a set of predetermined discrete angular orientations of the tracking array relative to the first clamp body;
  - a first fastener comprising a pair of slots extending within a side wall of the first clamp body from an end of the first clamp body to respective exits on sides of the first clamp body, and a pair of deformable tabs adjacent the respective exits, each deformable tab including one or more teeth; and
  - a first clamping surface; and
- a second clamp body having:
  - a second fastener complementary with the first fastener, the second fastener comprising a pair of tongues configured to be inserted into the pair of slots, each tongue having a serrated outer surface configured to engage with the teeth of the deformable tabs to permit insertion of the tongues into the slots and to resist withdrawal of the tongues from the slots absent outward deformation of the deformable tabs; and
  - a second clamping surface configured, when the second clamp body is coupled with the first clamp body, to define a clamping jaw for retaining an instrument; and wherein the tracking array includes a protrusion configured to selectively engage a selected one of the radial guide grooves to maintain the tracking array at a selected one of the predetermined discrete angular orientations.

2. The apparatus of claim 1, wherein the predetermined discrete angular orientations comprise six orientations separated by about 60 degrees.

3. The apparatus of claim 1, wherein each deformable tab is configured to be pulled outward to disengage the teeth from the serrated outer surface of the respective tongue to permit removal of the tongue from the slot.

4. The apparatus of claim 1, wherein the first clamping surface includes at least one pair of inclined surfaces configured to engage instruments having different diameters.

5. The apparatus of claim 1, further comprising a fastener extending through an aperture of the tracking array and into an anchor retained in a chamber of the first clamp body to affix the tracking array to the mounting surface.

6. The apparatus of claim 5, wherein the fastener comprises a bolt, and the anchor comprises a nut configured to receive the bolt.

7. The apparatus of claim 5, further comprising a cap coupled to a head of the fastener to facilitate toolless tightening and loosening of the fastener.

8. The apparatus of claim 1, wherein the protrusion comprises a rib on a body of the tracking array receivable within the radial guide grooves.

9. The apparatus of claim 1, wherein at least one of the first clamp body and the second clamp body is manufactured via injection molding or 3D printing.

10. The apparatus of claim 1, wherein the clamping jaw is configured to removably affix the tracking array to a surgical instrument to define a fixed spatial relationship between the tracking array and the instrument.

11. A mounting device for a tracking array, the mounting device comprising:
- a first clamp body having:
  - a mounting surface configured to support the tracking array, the mounting surface including a plurality of radial guide grooves arranged about an axis of the first clamp body, the radial guide grooves configured to define a set of predetermined discrete angular orientations of the tracking array relative to the first clamp body;
  - a first fastener comprising a pair of slots extending within a side wall of the first clamp body from an end of the first clamp body to respective exits on sides of the first clamp body, and a pair of deformable tabs adjacent the respective exits, each deformable tab including one or more teeth; and
- a first clamping surface; and
- a second clamp body having:
  - a second fastener complementary with the first fastener, the second fastener comprising a pair of tongues configured to be inserted into the pair of slots, each tongue having a serrated outer surface configured to engage with the teeth of the deformable tabs to permit insertion of the tongues into the slots and to resist withdrawal of the tongues from the slots absent outward deformation of the deformable tabs; and
  - a second clamping surface configured, when the second clamp body is coupled with the first clamp body, to define a clamping jaw for retaining an instrument.

12. The mounting device of claim 11, wherein the mounting surface is configured to receive the tracking array at any selected one of the predetermined discrete angular orientations to mitigate interference with an operator holding the instrument.

* * * * *